(12) United States Patent
Douglade et al.

(10) Patent No.: US 9,719,954 B2
(45) Date of Patent: Aug. 1, 2017

(54) METHOD FOR DETECTING AND DOSING HYDROFLUORIC ACID IN AN ELECTROLYTE CONTAINING LITHIUM HEXAFLUOROPHOSPHATE LIPF6 FOR LITHIUM BATTERIES

(71) Applicant: RENAULT s.a.s., Boulogne-Billancourt (FR)

(72) Inventors: Gregory Douglade, Grenoble (FR); Jean-Frederic Martin, Grenoble (FR)

(73) Assignee: RENAULT s.a.s., Boulogne-Billancourt (FR)

( * ) Notice: Subject to any disclaimer, the term of this patent is extended or adjusted under 35 U.S.C. 154(b) by 332 days.

(21) Appl. No.: 14/427,777

(22) PCT Filed: Sep. 13, 2013

(86) PCT No.: PCT/FR2013/052105
§ 371 (c)(1),
(2) Date: Apr. 23, 2015

(87) PCT Pub. No.: WO2014/041314
PCT Pub. Date: Mar. 20, 2014

(65) Prior Publication Data
US 2015/0226690 A1    Aug. 13, 2015

(30) Foreign Application Priority Data

Sep. 14, 2012  (FR) ..................... 12 58658

(51) Int. Cl.
G01N 27/30   (2006.01)
G01N 5/02    (2006.01)
G01G 3/16    (2006.01)
H01M 10/42   (2006.01)
H01M 10/052  (2010.01)

(52) U.S. Cl.
CPC ............. *G01N 27/30* (2013.01); *G01G 3/16* (2013.01); *G01N 5/02* (2013.01); *H01M 10/42* (2013.01); *H01M 10/052* (2013.01)

(58) Field of Classification Search
CPC ............ G01N 27/30; G01N 5/02; G01G 3/16; H01M 10/42; H01M 10/052
See application file for complete search history.

(56) References Cited

PUBLICATIONS

C. G. Barlow, "Reaction of Water and Hexafluorophosphates and with Li Bis(perfluoroethylsulfonyl)imide Salt" Electrochemical and Solid-State Letters, vol. 2, No. 8, 1999, p. 362-364.*
International Search Report issued Jan. 2, 2014 in PCT/FR2013/052105.
Xueyuan Zhang, et al., "Identity of Passive Film Formed on Aluminum in Li-Ion Battery Electrolytes with $LiPF_6$" Journal of the Electrochemical Society, vol. 153, No. 9, XP055070505, Jan. 1, 2006, pp. B344-B351.
Masayuki Morita, et al., "Anodic behavior of aluminum in organic solutions with different electrolytic salts for lithium ion batteries" Electrochimica Acta, vol. 47, No. 17, XP004366601, Jul. 5, 2002, pp. 2787-2793.
Tetsuya Kawamura, et al., "Decomposition reaction of $LiPF_6$-based electrolytes for lithium ion cells" Journal of Power Sources, vol. 156, No. 2, XP025083965, Jun. 1, 2006, pp. 574-554.

* cited by examiner

*Primary Examiner* — J. Christopher Ball
(74) *Attorney, Agent, or Firm* — Oblon, McClelland, Maier & Neustadt, L.L.P.

(57) ABSTRACT

A method for detecting and dosing hydrofluoric acid content of an electrolyte containing lithium hexafluorophosphate LiPF6 in lithium batteries, including measuring a variation in weight of a material that can undergo a surface reaction with the hydrofluoric acid in the electrolyte, the variation being determined by a quartz microbalance.

10 Claims, 1 Drawing Sheet

—— y = 1.2169 + 0.66707 x R² = 0.94241

—— y = 1.2715 + 0.11986 x R = 0.99183

METHOD FOR DETECTING AND DOSING HYDROFLUORIC ACID IN AN ELECTROLYTE CONTAINING LITHIUM HEXAFLUOROPHOSPHATE LIPF6 FOR LITHIUM BATTERIES

The present invention relates to a process for detecting and assaying the content of hydrofluoric acid present within an electrolyte based on lithium hexafluorophosphate $LiPF_6$ in lithium batteries carried out from the measurement of the variation in weight of a material capable of reacting at the surface with the hydrofluoric acid within the electrolyte which is determined using a quartz crystal microbalance.

Lithium batteries occupy an increasingly important place in the electrical energy storage market. This is because their current performance, in particular with regard to the storage of electrical energy, outstrips by far the older technologies based on nickel batteries, such as nickel-metal hydride NiMH batteries or nickel-cadmium NiCd batteries.

Among lithium batteries, lithium-ion batteries are rechargeable batteries which are particularly interesting as they can advantageously be used as energy source in portable electronic devices, such as mobile telephones and laptops, in particular by virtue of their low cost price, or in the field of motor vehicles, such as in electric cars.

Lithium-ion batteries generally comprise a positive electrode, composed in particular of lithiated transition metal oxides of $Li(Ni, Mn, Co, Al)O_2$ type, such as lithiated cobalt dioxide $LiCoO_2$, a negative electrode, composed in particular of carbon-based materials, such as graphite, and an electrolyte which separates the positive electrode from the negative electrode. The electrolyte is impregnated in a porous separator and is composed of a mixture of carbonates and of a lithium salt, in particular lithium hexafluorophosphate $LiPF_6$.

The lithium ions thus move within the electrolyte between the negative electrode and the positive electrode in order to generate an electric current. In particular, the lithium ions move from the negative electrode toward the positive electrode during the discharging of the battery and from the positive electrode toward the negative electrode during the recharging of the battery.

The technology of lithium-ion batteries is based very largely on the use of lithium hexafluorophosphate $LiPF_6$, which provides a noteworthy performance in terms of conductivity, viscosity and cost. However, lithium hexafluorophosphate generally exhibits a major disadvantage which lies mainly in its chemical instability.

This is because lithium hexafluorophosphate often decomposes, giving rise to the appearance of lithium fluoride LiF and phosphorus pentafluoride $PF_5$ according to the following mechanism:

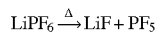

The presence of phosphorus pentafluoride within the electrolyte then contributes, in the presence of water molecules, to generating hydrofluoric acid HF and phosphorus oxyfluoride $OPF_3$ according to the following reaction:

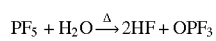

The presence of these by-products and in particular of hydrofluoric acid within the electrolyte can cause major problems with regard to the safety, durability and recycling of the lithium-ion battery. In particular, the presence of the hydrofluoric acid causes problems of toxicity and its action, along with that of the phosphorus pentafluoride and that of the phosphorus oxyfluoride, catalyzes the decomposition of the electrolyte and also the deterioration in the overall performance and the lifetime of the battery. The decomposition of the electrolyte can in particular result, on the one hand, in the formation of a solid electrolyte interface (SEI) between the electrode and the electrolyte and, on the other hand, in the formation of by-products harmful to the operation of the battery. Furthermore, the positive electrode can also dissolve in the presence of the acidic molecules generated by the decomposition of the phosphorus pentafluoride.

The result of this is that it proves to be important to be able to quantify the presence of hydrofluoric acid within the electrolyte during its storage in order to avoid the operating problems encountered in lithium-ion batteries.

In order to overcome the abovementioned disadvantages, provision has already been made to employ an acid/base assaying method targeted at assaying the content of hydrofluoric acid present in the electrolyte based on lithium hexafluorophosphate. However, such a method requires withdrawing a sample within the electrolyte, which implies that the content of hydrofluoric acid is only measured at a given time and in ex situ fashion.

Furthermore, provision has also been made, by means of the international patent application WO 2004/104579, for a process for detecting fluoride or hydrogen fluoride in a sample which employs a silylated organic compound which undergoes a desilylation reaction when it is in the presence of hydrofluoric acid. The appearance of the desilylated organic compound or the disappearance of the silylated organic compound is subsequently detected and/or assayed by means of gas chromatograpy or detection and/or assaying carried out by means of an immunological test. The assaying of these compounds then makes it possible to deduce the content of hydrofluoric acid present in the sample.

International patent application WO 2009/113994 has, for its part, provided a process for detecting hydrofluoric acid in an aqueous and acidic medium present during the preparation of the surface of semiconductors.

These documents describe processes which are not suitable for the detection of hydrofluoric acid in electrolytes which comprise lithium hexafluorophosphate and which are employed in lithium batteries.

In the light of the above, the aim of the invention is to provide a process which makes it possible to detect and measure, over time, the content of hydrofluoric acid present within an electrolyte based on lithium hexafluorophosphate $LiPF_6$, that is to say to assay in situ the content of hydrofluoric acid, in order to be able to limit, indeed even eliminate, the operating problems encountered in lithium batteries which were mentioned above.

To this end, it has been found that, by employing a process in which the variation in the weight of a layer (a), comprising a material M capable of reacting at the surface with the hydrofluoric acid HF present within an electrolyte based on lithium hexafluorophosphate $LiPF_6$, is measured using a quartz crystal microbalance, it is possible not only to detect but also to directly and effectively assay, over time, the content by weight of hydrofluoric acid present within the electrolyte in lithium batteries.

The process according to the invention consists in particular in bringing the electrolyte based on lithium hexafluorophosphate $LiPF_6$ into contact with a layer (a) comprising a material M capable of reacting, at the surface, with the hydrofluoric acid HF which results from the decomposition of the phosphorus pentafluoride $PF_5$ according to the above-mentioned reaction. The material M of the layer (a) thus reacts with the hydrofluoric acid HF to form, at the surface, a layer (b) composed of a fluorinated compound having the structure $MF_n$, with n corresponding to an integer strictly greater than 0.

The formation of the layer (b) at the surface of the layer (a) results in a variation in the weight of the layer (a) which is measured by means of a quartz crystal microbalance. In particular, the layer (a) is deposited on an electrode of the quartz crystal microbalance which measures the variation in weight of said layer which makes it possible to deduce the content of hydrofluoric acid which has reacted with the material of the layer (a) and consequently the content by weight of hydrofluoric acid present within the electrolyte.

In other words, the process is based in particular on the surface reactivity of materials, capable of reacting at the surface with hydrofluoric acid, which are deposited on an electrode of a quartz crystal microbalance.

Thus, the process in accordance with the present invention makes it possible to determine in situ the content of hydrofluoric acid at a given moment and also its change over time.

The detecting and assaying process thus employed therefore makes it possible to be able to detect and minimize the operating problems encountered within lithium batteries which are due to the presence of hydrofluoric acid within the electrolyte.

A subject matter of the present invention is thus in particular a process for detecting and assaying the content of hydrofluoric acid in an electrolyte based on lithium hexafluorophosphate $LiPF_6$ in lithium batteries, comprising the following stages:
(i) bringing said electrolyte into contact with a layer (a) comprising a material M capable of reacting at the surface with hydrofluoric acid HF, the hydrofluoric acid originating from the reaction between lithium hexafluorophosphate and water,
(ii) measuring the variation in weight of the layer (a) by bringing said layer (a) into contact with an electrode of a quartz crystal microbalance, the variation in weight of the layer (a) being due to the reaction between the material M of the layer (a) and the hydrofluoric acid HF to form, at the surface, a layer (b) comprising a fluorinated compound having the structure $MF_n$, with n corresponding to an integer strictly greater than 0;
(iii) calculating the content by weight of hydrofluoric acid from the variation in weight of the layer (a) determined in stage (ii).

According to one embodiment of the invention, the process also comprises a stage of calculating the amount of water present within the electrolyte.

According to the invention, stage (iii) of the calculation by weight of hydrofluoric acid is carried out by comparison with nomograms drawn up starting from electrolytic solutions of known titration.

Thus, the variation in weight of the layer (a) can be measured on several occasions over time with an electrode of a quartz crystal microbalance, which makes it possible to determine the content by weight of hydrofluoric acid over time which is present in the electrolyte.

The process according to the invention thus makes it possible to accurately measure the content of hydrofluoric acid.

Other subject matters, characteristics, aspects and advantages of the invention will become even more clearly apparent on reading the description and examples which follow.

In accordance with the present invention, the layer (a) comprises a material M capable of reacting at the surface with the hydrofluoric acid present in the electrolyte based on lithium hexafluorophosphate $LiPF_6$.

Preferably, the layer (a) comprises solely a material M capable of reacting at the surface with hydrofluoric acid. In this case, preferably, the layer (a) is shaped into a part of strip or disk type exhibiting a high surface area and a low thickness.

According to one embodiment, the material M of the layer (a) is chosen from the elements of the following Groups IIIa, IIIb and Ib of the Periodic Table of the Elements.

Preferably, the material of the layer (a) is chosen from aluminum, boron and silicon.

Preferably, the material M of the layer (a) is chosen from the elements of Groups IIIa and IIIb of the Periodic Table of the Elements.

More preferably, the material of the layer (a) is chosen from aluminum, boron and silicon and in particular aluminum and silicon.

Thus, the layer (a) can be a layer of aluminum or of silicon. In accordance with the invention, the layer (b) formed is not soluble in the electrolyte.

More preferably still, the material of the layer (a) is chosen from the metals of Group IIIa appearing in the Periodic Table of the Elements.

According to a more particularly preferred embodiment, the material of the layer (a) corresponds to aluminum.

Thus, the layer (a) employed in the process in accordance with the present invention is more particularly a layer of aluminum.

The layer (a) comprising a material capable of reacting at the surface with hydrofluoric acid can exhibit a thickness ranging from 5 nm to 100 μm and preferably a thickness ranging from 5 nm to 200 nm.

The layer (a) can also comprise a surface area ranging from 0.1 to 10 $cm^2$ and preferably ranging from 1 to 5 $cm^2$.

Preferably, the layer (a) corresponds to a disk of aluminum which can exhibit a surface area of 1.53 $cm^2$.

In accordance with the present invention, the process comprises a stage consisting in bringing the electrolyte into contact with the layer (a) comprising the material M capable of reacting, at the surface, with the hydrofluoric acid which originates from the reaction between the lithium hexafluorophosphate and the water.

According to one embodiment, the layer (a) of material M is deposited on an electrode of a quartz crystal microbalance which is subsequently brought directly into contact with the electrolyte by immersion of the electrode in said electrolyte.

In other words, the electrode of the quartz crystal microbalance is covered with the layer (a) defined above and is brought directly into contact by immersion in the electrolyte.

In accordance with this embodiment, the measurement of the variation in weight of the layer (a) is carried out directly within the electrolyte on several occasions, so as to determine the change in the content by weight of hydrofluoric acid over time within the electrolyte.

By extension, a calculation of the variation in the content of water in the electrolyte is possible.

The measurement can be restarted with the same electrode if, in the meantime, said electrode is properly rinsed with water and with acetone until the layer (a) has been completely removed.

According to another embodiment, the layer (a) is first weighed on an electrode of a quartz crystal microbalance and then said layer (a) is immersed in the electrolyte. After a time necessary for the reaction between the hydrofluoric acid and the material of the layer (a), said layer (a) is deposited on the electrode of the quartz crystal microbalance in order to measure the variation in weight of the layer (a).

In particular, the electrolyte comprising the layer (a) is withdrawn so as to be able to measure the weight of the layer (a).

In accordance with this embodiment, the measurement of the variation in weight of the layer (a) is carried out subsequent to the withdrawal of a portion of the electrolyte comprising the layer (a) and can be carried out on several occasions so as to determine the content by weight of hydrofluoric acid over time within the electrolyte.

In accordance with the present invention, the material of the layer (a) reacts with the hydrofluoric acid present in the electrolyte in order to form, at the surface of said layer (a), a layer (b) comprising a fluorinated compound having the structure $MF_n$, with n corresponding to an integer strictly greater than 0 and M corresponding to the material of the layer (a).

In particular, when the material of the layer (a) is chosen from aluminum, boron and silicon, then the layer (b) comprises a fluorinated compound having the structure $MF_n$, with M corresponding to an element chosen from aluminum, boron and silicon and n corresponding to an integer ranging from 1 to 4.

According to a preferred embodiment, when the layer (a) is a layer of aluminum or silicon, then the layer (b) is a layer of aluminum fluoride $AlF_3$ or of silicon tetrafluoride $SiF_4$.

Preferably, the layer (b) is a layer of aluminum fluoride $AlF_3$.

According to a preferred embodiment, the layer (a) corresponds to a layer of aluminum and the layer (b), obtained at the surface of the layer (a) subsequent to the reaction between the aluminum and the hydrofluoric acid, is a layer of aluminum fluoride $AlF_3$.

The formation of the layer (b) at the surface of the layer (a) can be observed by means of scanning electron microscopy (SEM). In other words, scanning electron microscopy shows that a surface reaction has actually taken place between the hydrofluoric acid and the material of the layer (a).

Furthermore, the chemical nature of the layer (b) formed at the surface of the layer (a) can be determined by means of an X-ray spectrum, in particular via an energy dispersive X-ray analysis EDX.

The formation of the layer (b) at the surface of the layer (a) thus brings about a variation in the weight of the layer (a), more particularly an increase in the weight of the layer (a).

The variation in the weight of the layer (a) is determined by means of a quartz crystal microbalance.

In particular, the layer (a) is deposited on an electrode of the quartz crystal microbalance and the variation in weight of said layer (a) will bring about a variation in the resonant frequency of the quartz. This is because the variation in weight of the layer (a) on the electrode will result in a movement of the quartz, thus causing a shift with regard to its resonant frequency.

In other words, the electrode of the quartz crystal microbalance measures the variation in frequency brought about by the variation in the weight of the layer (a). The measurement of the variation in frequency thus makes it possible to determine the variation in weight of the layer (a).

Thus, the variation in the weight of the layer (a) is determined from the variation in the frequency of the quartz crystal microbalance in accordance with the following equation:

$$\Delta f = \frac{-2\Delta m \times f_0^2}{A \times \sqrt{\rho_q \times \mu_q}}$$

in which:

$\Delta f$ corresponds to the variation between the resonant frequency of the quartz induced by the layer (a) before reaction with the hydrofluoric acid and the resonant frequency of the quartz induced by the layer (a) after reaction with the hydrofluoric acid, $\Delta m$ corresponds to the variation in weight between the layer (a) before reaction with the hydrofluoric acid and the layer (a) after reaction with the hydrofluoric acid, $f_0$ corresponds to the intrinsic resonant frequency of the quartz, $\rho_q$ corresponds to the density of the quartz, $\mu_q$ corresponds to the shear modulus of the quartz, A corresponds to the active surface area of the quartz between the electrodes and the quartz crystal microbalance.

The variation in weight of the layer (a) makes it possible to determine the weight of the layer (b) formed, which makes it possible to deduce the content by weight of hydrofluoric acid which has reacted with the material of the layer (a) and consequently the content by weight of hydrofluoric acid present within the electrolyte.

The calibration of the quartz crystal microbalance can be carried out with the use of standardized and certified solutions in a medium equivalent to that studied, without lithium hexafluorophosphate. Nomograms are thus specifically produced for each medium studied.

Other characteristics and advantages of the invention will become apparent on the detailed examination of an embodiment taken by way of example of a process for detecting and assaying hydrofluoric acid within an electrolyte based on $LiPF_6$ and illustrated by the appended drawings, in which.

Four aluminum disks having a surface area of 1.53 $cm^2$ were prepared from aluminum sheets intended to act as current collector. These disks were washed, dried and then weighed with a quartz crystal microbalance. Each sample was subsequently immersed in an electrolyte as described below.

The electrolyte studied corresponds to a 1 mol·$l^{-1}$ solution of $LiPF_6$ dissolved in a carbonate mixture of EC (1), PC (1) and DMC (3) type. In a glove box, 10 ml of the solution are introduced into four plastic flasks; each amount of electrolyte is carefully and accurately weighed. A sample as mentioned above is introduced into each flask.

An increasing amount of water is introduced into each flask using a 5 μl micropipette, in particular 4, 9, 15 and 22 mg of water, and also a control solution without addition of water.

The lithium hexafluorophosphate thus reacts according to the following reaction:

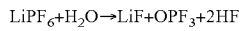

The solutions are subsequently placed in a desiccator filled with dehydrating agent (silica gel) which has been dried beforehand, for 7 days; the desiccator is placed under reduced pressure the time of the experiment for 24 hours.

At the end of this period, the aluminum disks are removed from the electrolyte and are rinsed with dimethyl carbonate and then with acetone and are dried at 60° C. for 24 hours. Once dry, the disks are again weighed using the quartz crystal microbalance.

Figure 1:
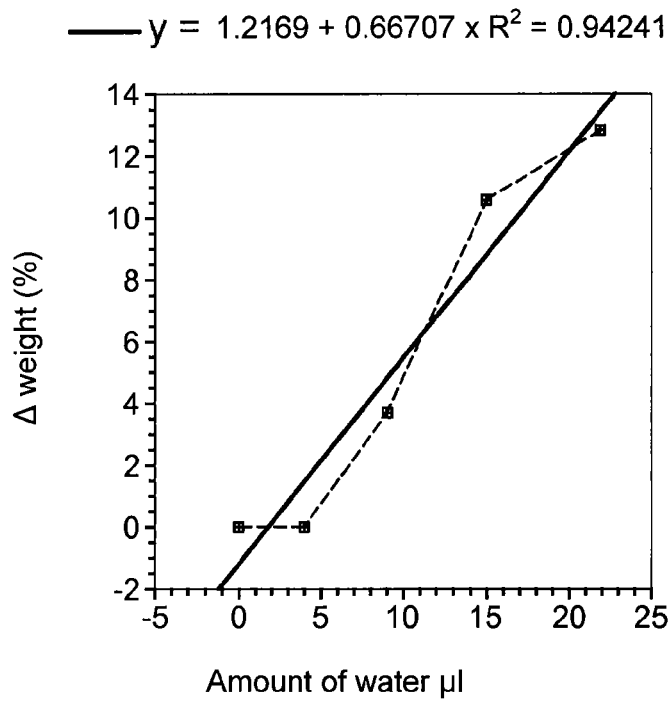
FIG. 1 represents a graph in which the variation in weight of the layer (a) has been represented as a function of the amount of water for contents ranging from 0 to 25 μl.

As shown in FIG. 1, the variation in weight of the aluminum disk is proportional to the amount of water introduced.

The results of the variation in weight of the aluminum disks are shown in the following table:

| Number of the sample | Weight of aluminum (mg) before reaction | Weight of aluminum (mg) after reaction | Variation in the weight of the aluminum disks in mg |
|---|---|---|---|
| 1 | 8.413 | 8.415 | 0.002 |
| 2 | 8.369 | 8.681 | 0.312 |
| 3 | 8.389 | 9.279 | 0.89 |
| 4 | 8.395 | 9.473 | 1.078 |

Figure 2:
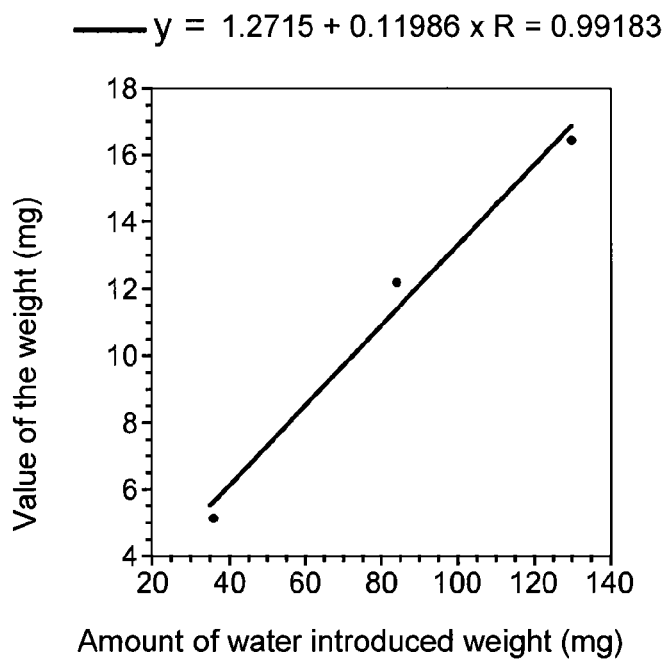
FIG. 2 represents a graph in which the variation in weight of the layer (a) has been represented as a function of the amount of water for contents ranging from 35 to 130 μl.

Other tests were carried out with greater amounts of water ranging from 35 to 130 μl and a linear behavior was also observed here, as shown in FIG. 2.

The visual observation of the aluminum disks indicates that the surface has indeed been modified, given that the presence of a white surface on the disks is found.

Furthermore, the photographs taken using scanning electron microscopy (SEM) prove that a surface reaction has taken place.

The EDX analysis indicates that the chemical nature of the compounds formed is of the $AlF_3$ type, which clearly confirms the surface reaction at the surface of the electrode of the quartz crystal microbalance.

The experiment shows that a linear law exists between the amount of water present in the electrolyte and the increase in weight of the layer a. Consequently, for a person skilled in the art, it is sufficient to draw up nomograms which make it possible, by simple confirmation of the weight of the layer b, to go back to the amount of water and of hydrofluoric acid in the electrolyte.

The invention claimed is:

1. A process for detecting and assaying hydrofluoric acid in an electrolyte based on lithium hexafluorophosphate $LiPF_6$, comprising:
   (i) bringing the electrolyte into contact with a first layer comprising a material M that reacts at a surface with hydrofluoric acid HF, the hydrofluoric acid originating from the reaction between lithium hexafluorophosphate and water;
   (ii) measuring variation in weight of the first layer by bringing the first layer into contact with an electrode of a quartz crystal microbalance, the variation in weight of the first layer being due to the reaction between the material M of the first layer and the hydrofluoric acid HF to form, at a surface, a second layer comprising a fluorinated compound having the structure $MF_n$, with n corresponding to an integer strictly greater than 0;
   (iii) calculating the content by weight of hydrofluoric acid from the variation in weight of the first layer determined in (ii).

2. The process as claimed in claim 1, further comprising (iv) determining an amount of water in the electrolyte.

3. The process as claimed in claim 1, wherein the material M of the first layer is chosen from elements of Groups IIIa, IIIb and Ib of the Periodic Table of the Elements.

4. The process as claimed in claim 1, wherein the material M of the first layer is chosen from aluminum, boron, and silicon.

5. The process as claimed in claim 1, wherein the material M of the first layer is chosen from metals of Group IIIa of the Periodic Table of the Elements.

6. The process as claimed in claim 1, wherein the first layer is a layer of aluminum.

7. The process as claimed in claim 1, wherein the material M of the first layer is chosen from aluminum, boron and silicon, and the second layer comprises a fluorinated compound having the structure $MF_n$, with M corresponding to an element chosen from aluminum, gold, boron and silicon and n corresponding to an integer ranging from 1 to 4.

8. The process as claimed in claim 6, wherein the second layer is a layer of aluminum fluoride $AlF_3$ or a layer of silicon tetrafluoride $SiF_4$.

9. The process as claimed in claim 1, wherein the first layer is deposited on an electrode of a quartz crystal microbalance which is subsequently brought directly into contact with the electrolyte by immersion of the electrode in the electrolyte to measure the variation in weight of the first layer.

10. The process as claimed in claim 1, wherein the first layer is weighed on an electrode of a quartz crystal microbalance, then immersed in the electrolyte and, after a time necessary for the reaction between the hydrofluoric acid and the material of the first layer, the first layer is deposited on the electrode of the quartz crystal microbalance to measure the variation in weight of the first layer.

* * * * *